United States Patent [19]

Trautmann

[11] Patent Number: 4,519,243

[45] Date of Patent: May 28, 1985

[54] APPARATUS FOR THE NONDESTRUCTIVE TESTING OF ELONGATED TEST SPECIMENS BY MAGNETIC TECHNIQUES

[75] Inventor: Wolfgang Trautmann, Reutlingen, Fed. Rep. of Germany

[73] Assignee: Institut Dr. Friedrich Forster Prufgeratebau GmbH & Co. KG., Reutlingen, Fed. Rep. of Germany

[21] Appl. No.: 473,952

[22] Filed: Mar. 10, 1983

[30] Foreign Application Priority Data

Mar. 12, 1982 [DE] Fed. Rep. of Germany ....... 3209006

[51] Int. Cl.³ ..................... G01M 19/00; G01N 37/00
[52] U.S. Cl. .................................................. 73/432 R
[58] Field of Search ............ 73/432 B, 432 R, 432 V, 73/637, 638, 640, 635, 622; 324/261, 262

[56] References Cited

U.S. PATENT DOCUMENTS 3,263,809 8/1966 Mandula et al. ................. 209/941 X
3,894,425 7/1975 Winters et al. .................... 73/622 X
4,258,319 3/1981 Shimada et al. ................ 324/622 X

FOREIGN PATENT DOCUMENTS 2489502 3/1982 France .................................. 324/262
111881 9/1979 Japan ...................................... 73/637
113951 9/1980 Japan .................................... 324/262

Primary Examiner—Jerry W. Myracle
Assistant Examiner—Tom Noland

[57] ABSTRACT

The devices for holding down a speciman to be tested are arranged on the same side of the tube as the transducer, without the tube movement being obstructed. The holding down devices may be arranged directly opposite to the rotation devices, or optionally in the immediate neighborhood thereof. Bending of the tube due to the holding devices does not occur even where relatively large pressing forces are used.

8 Claims, 3 Drawing Figures

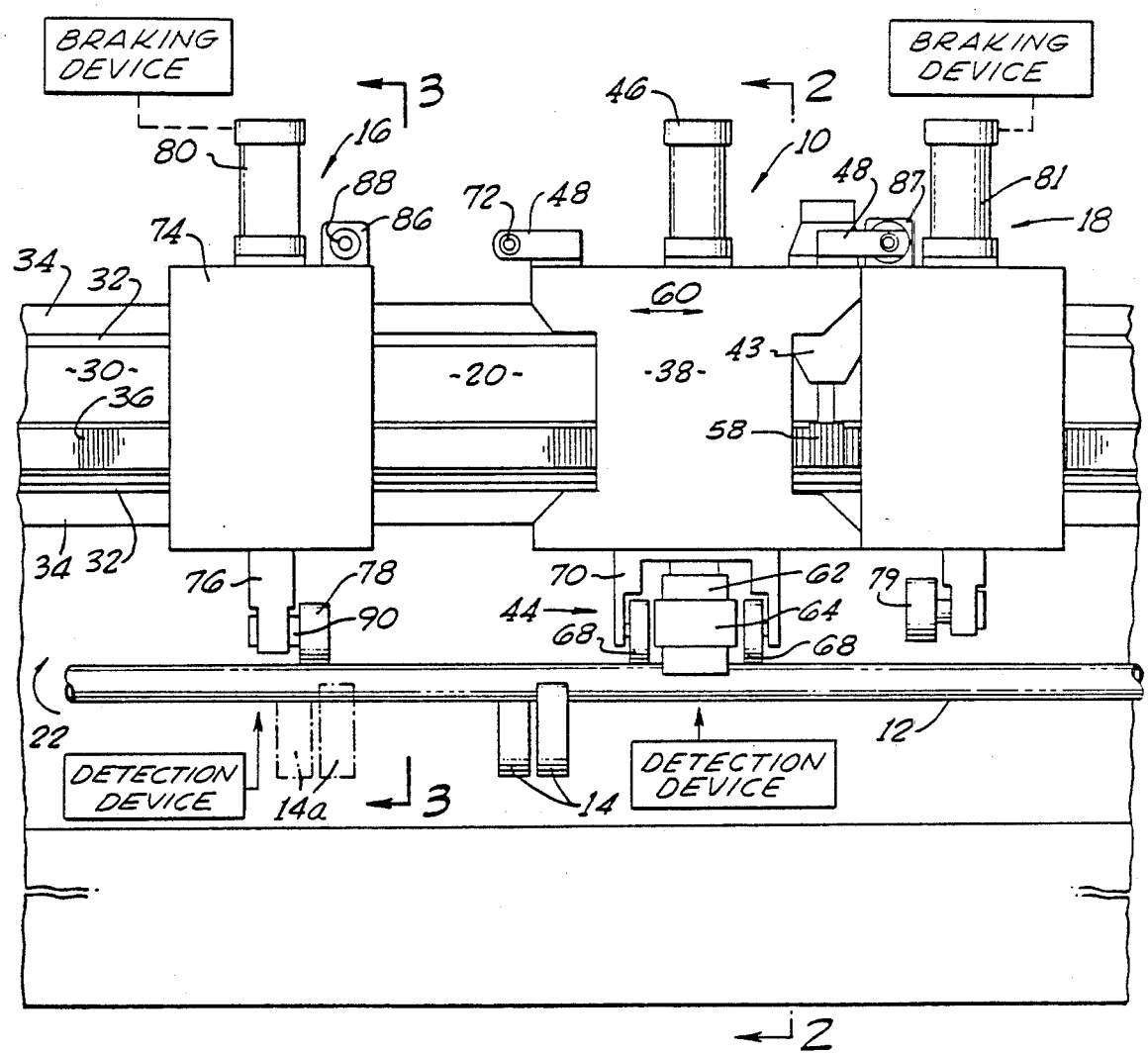
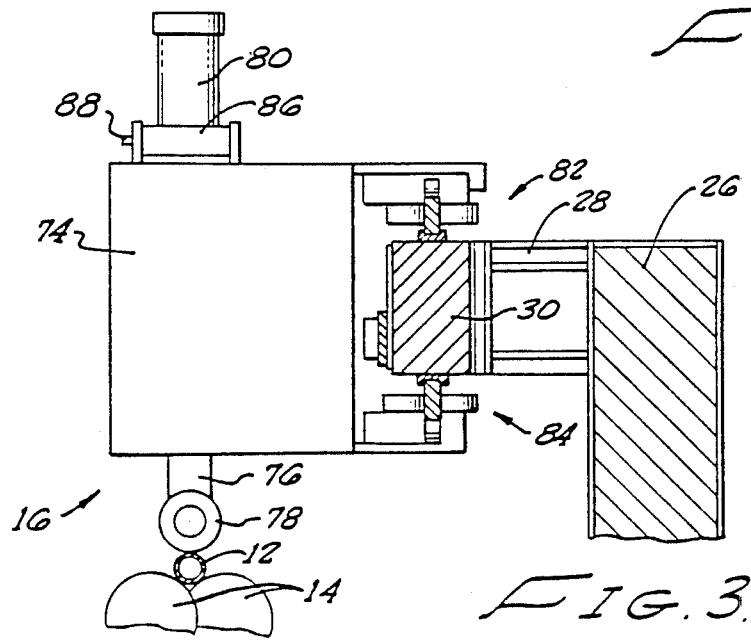
FIG. 1.
FIG. 3.

APPARATUS FOR THE NONDESTRUCTIVE TESTING OF ELONGATED TEST SPECIMENS BY MAGNETIC TECHNIQUES

The present invention relates generally to apparatus for the nondestructive testing of elongated test specimens and, more particularly, to such apparatus especially adapted for the testing of test specimens having essentially circular cross-section such as a tube.

BACKGROUND OF THE INVENTION

Testing apparatus is known, in which a tube to be tested rests on a number of turning rollers and is brought to rotation about its longitudinal axis by the rollers. In a carrier arrangement, two longitudinally movable transducer blocks are suspended and supported by the tube for running along a testing track in longitudinal direction of the tube. The transducers incorporated in the transducer blocks detect along helical curves of the surface of the rotating tube. In such an arrangement, it is disadvantageous that a pressing of the tube on the rollers be effected solely by the weight of the tube and the transducer blocks. If sufficient pressure is exerted by a transducer block, then an especially thin tube will bend appreciably, if the transducer block is located in the middle between two turning rollers. This results in strong radial movements and to an unsteady running of the tube. In U.S. Pat. No. 3,263,809, a testing device is described, in which a tube to be tested rests on turning rollers arranged transversely to the axis of the tube and is driven by those rollers in a helical movement, while the surface of the tube is scanned by stationary probes. Opposite to the turning rollers, devices for holding and pressing the tube onto the turning rollers are provided. Thus, they hold the tubes (which are frequently bent) in steady contact with the pressure rollers and prevent undesirable movements of the tube in radial directions. A uniform turning movement of the tube, being particularly desirable for electronic processing, is only guaranteed by a steady contact between the tube and turning rollers.

The utilization of devices for holding down the test specimen was either not possible up to now or only possible under great difficulties for the first described known testing apparatus, as stationary devices for holding the test specimen down would obstruct the longitudinal movement of the transducer blocks. The apparatus for holding down the test specimen, therefore, would have to be moved to the side, whenever a transducer block is to pass it, and this would have to be done very quickly, which would be difficult.

Furthermore, stationary, tiltable devices for holding down a test specimen located laterally to the specimen are not feasible even when the loading of the testing device is to be performed from the side. It is true that testing devices are known in which the scanning of a tube is performed from below by longitudinally moved transducers, and for which, thus, stationary devices on the upper side of the tube for holding down the tube are possible. These may be used, however, only for larger tube diameters, where there is enough space between two driving rollers for passage of a transducer block. Testing devices for relatively thin wall tubes and/or small diameter tubes cannot make use of the described scanning of the underside of the tube.

SUMMARY OF DESCRIBED APPARATUS

The invention offers a solution for the testing device of the previously described kind, in which the devices for holding down the specimen are arranged on the same side of the tube as the transducer device, without the movement of which being obstructed. The expenditure for the solution according to the invention remains within reasonable limits, as the guiding device being present is also used for the devices for holding down the specimen. The effectiveness of the devices for holding down is an optimum, however, for they may be arranged directly opposite to the rotation devices or in the immediate neighborhood thereof. Bending of the tube due to the devices for holding it down does not occur even in the case of relatively large pressing forces. A quiet uniform turning movement of the tube with minimum transversal movement is guaranteed.

DESCRIPTION OF THE DRAWINGS

FIG. 1 is a side elevational view of testing apparatus with a transducer and two apparatus for holding down a test specimen.

FIG. 3 is an end elevational view of a device for holding the test specimen against support rollers.

DESCRIPTION OF A PREFERRED EMBODIMENT

Figure 2:
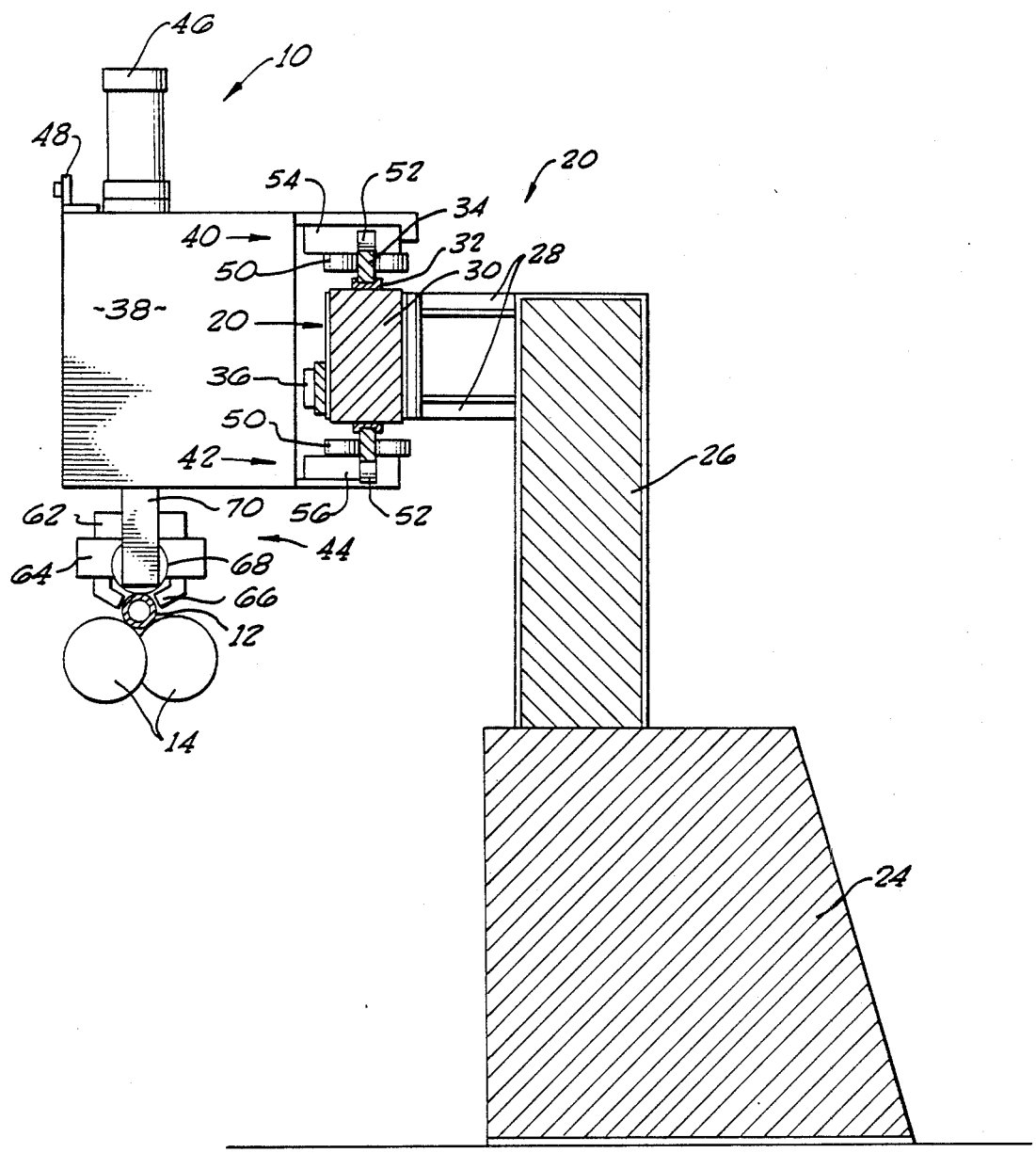
FIG. 2 is an end elevational view of the transducer device taken along line 2—2 of FIG. 1.

In a simplified representation, FIGS. 1 and 2 show a transducer 10 for non-destructive testing of a tube 12, the tube resting on a number of roller pairs (one only is shown). Two sets of apparatus 16 and 18 for holding down the tube 12 are of identical construction and serve to press the tube against the roller pairs 14. A guiding device 20 is a support member from which the transducer device 10 as well as the two devices 16 and 18 for holding down the tube are suspended. Of the roller pairs 14 carrying the tube 12, a portion may also be provided with a drive (not represented for simplicity reasons) suitable to bring the tube into rotation about the axis according to arrow 22.

The guiding device 20 has a series of supports 24 distributed along the testing track with studs 26 arranged on them having a guide bar 30 interconnected therewith via a connection member 28. To the upper and to the underside of the bar 30, one guide rail 34 each is mounted by profile pieces 32. To the side of the bar 30, a toothed rack 36 is attached, the task of which is explained further below. Instead of the toothed rack 36, a drive chain rigidly fixed to the bar 30 may be provided, also.

The transducer device 10 includes a base body 38, on which there are arranged upper and lower guiding means 40 and 42, designed in a similar way and being in running connection with the guide rails 34, a drive motor 43 for moving the transducer arrangement 10, a movable transducer system 44 for scanning the surface of the tube 12, a pressure cylinder 46 for lifting the transducer system 44 or for pressing it on to the tube 12, as the case may be, and coupling flaps 48 for rigid coupling of the devices 16 or 18 for holding down the tube to the transducer device 10. The guiding means 40 or 42 each consist of two horizontally arranged rollers 50 running on the front or the rear sides of the guide rails 34, and one vertically arranged roller 52 running along the upper or the lower side, respectively, of the guide rails. By bearing means 54 and 56, the upper and lower guide means 40 are connected to the base body 38. The reversible motor 43 drives a toothed wheel 58 which is in engagement with the toothed rack 36. It is capable, thus, to move the transducer device 10 in the direction of arrow 60 forward or backward.

Turning now to FIG. 2, the transducer system 44 is provided with all components necessary for a non-destructive testing of the tube 12. In the present example, a fault test according to the magnetic stray flux method is chosen, in the place of which, however, any other non-destructive fault testing technique may be taken. A magnet yoke 62 with operating windings 64 provides a sufficient magnetization of the tube 12. In the middle between the pole shoes 66, opposite to the ridge line of the tube, a probe shoe with a series of probes is arranged (not visible in the figures), serving for receiving the magnetic stray fluxes caused by faults in the tube, transforming them into corresponding electrical signals and transmitting them to an electrical evaluation unit. The transducer system 44 is supported during the test procedure by rollers 68 mounted in a frame 70 on the tube 12. The magnet yoke 62 and the probe shoe may be suspended movably in the frame 70 and abut against the tube 12 over rollers or sliding skids. The frame 70 and, thus, the complete transducer system 44 may be lifted from the tube 12 or may be lowered to the tube by means of the pressure cylinder 46. In the latter case, a pressure may be exerted on the tube 12 over the rollers 68, this pressure being adjustable by corresponding loading of the pressure cylinder 46, if need be. The coupling flaps 48 are fastened at the right and left to the top of the base body 38. The flaps are provided with bores 72 at their free ends each facing in the direction of one of the two devices for holding down the tube 16 and 18, respectively.

The two devices for holding down the tube 16 and 18 are symmetrical with respect to construction. It is only necessary therefore, to describe one of them in detail, e.g. the device 16, and which is represented once again in FIG. 3 in an end view. The major important components of the device 16 are: a carrying body 74 carrying the remaining parts of the device, a piston 76 with a roller 78 for contacting the tube, a pressure cylinder 80 for moving the piston 76, upper and lower guiding means 82 and 84 identical to the guiding means 40 and 42 and requiring, therefore, no further explanation, and a pressure cylinder 86 with a coupling bolt 88 actuated by the pressure cylinder. The roller 78 is connected to the piston 76 by an axle 90. By actuating the pressure cylinder 80, the roller 78 may be lifted from the tube 12 or may be lowered onto the tube. In the latter case, any desired pressure may be exerted on the tube 12 by the roller 78. The guiding means 82 and 84 are connected to the carrying body 74 in the same way as the guiding means 40 and 42 to the base body 38. Furthermore, the guiding means 82 and 84 interact with the guiding rails 34 in the same way as the guiding means 40 and 42. Correspondingly, the devices 16 and 18 for holding down the tube are movable along the tube 12 in the same path as the transducer device 10. The latter may take along on its path each of the two devices for holding down and move on forward or backward, as desired. To do this, it is only necessary to have the coupling bolt 88, actuated by the pressure cylinder 86, latch into the opening 72 and, thus, lock the transducer device 10 with one of the two devices for holding down the tube. FIG. 1 shows the device 18 for holding down the tube and transducer device 10 locked to each other in this way.

The described testing device operates in the following way. Tube 12 is rotated by the roller pair 14. The roller 78 of the device 16 for holding the tube down under influence of the pressure cylinder 80 presses the tube 12 onto the driving roller pair 14. In that way, it may be assumed that the lateral distance between roller 78 and the roller pair 14 is small compared to the distance between two adjacent roller pairs, so that the bending effectcaused by the pressing force remains very small. A braking device for the holding down device 16 causes the latter to remain in its position. Meanwhile, the transducer system is in the test position, that is, the rollers 68 rest on the tube 12, and the transducers are connected to the respective supply and evaluation units. The pressure exerted by the rollers 68 is such that there is no appreciable bending of the tube 12. The roller 79 for the holding down device 18 is maintained in the lifted-up position by the pressure cylinder 81.

In the case of continuous testing by the transducer system 44, the transducer device 10 together with the device 18 coupled to it moves toward the device 16 and is, according to the representation of FIG. 1, just about to strike against the latter. Immediately before abutting takes place, the braking device of the device 16 is released under control of a switching device (not shown). At the very moment of the abutting of the transducer device 10 against the device 16, a simple automatic control function effects coupling of the device 16 to the transducer device by the pressure cylinder 86, lifting of the roller 78 from the tube 12 by pressure cylinder 80, decoupling of the device 18 by pressure cylinder 87, lowering of the holding down roller 79 on the tube 12 at a position adjacent to the roller pair 14, and braking of the device 18 at this location. In doing this, the transducer device 10 continues its course without interruption of the test procedure, now carrying with it device 16 instead of the device 18. After scanning of the complete tube 12 or, if more than one transducer device is applied, after scanning of the assigned portion, the tube 12 is replaced by a second one. The test procedure now takes place in reverse order. After testing of the second tube, the transducer device 10 and the device 16 and 18 are back in their original positions again.

Alternatively to the described mode of operation, it may be provided, too, that the holding-down rollers are lowered each at the location of the suporting or driving roller pair. In this case, the roller pair 14A represented in dashed lines is applied instead of the roller pair 14. In the course of the test procedure, the transducer device 10 coming from the right and coupled with the holding down device 18 approaches the device 16 and the roller pair 14A. Again, shortly before the transducer device 10 abuts against the holding down device, the braking device of the latter is released. At the moment of contact, the coupling of the holding down device 16 to the transducer device 10 is effected by latching of the bolt 88 into the bore 72. Simultaneously, the transducer device 10 performs for a short time the pressing-on function of the device 16, the pressing roller 78 of which is brought into the lifted-up position by the pressure cylinder 80. In that way, by pressure increase in the cylinder 46, an increase of the pressing effect of the rollers can be performed. The course of the transducer device 10, now with two lifted-up devices 16 and 18, is continued meanwhile in an undisturbed manner, and as well the testing activities. As soon as the pressing roller 79 of the device 18 is at the location of the roller pair 14A, the device 18 is decoupled by the pressure cylinder 87 from the transducer device 10. Pressure cylinder 81 lowers the pressing-on roller 79, taking over in that way the pressing function for the tube 12. At the same time, the braking device of the device 18 is activated. The pressure of the pressure cylinder 46 may be reduced again, in case it had been increased before. The transducer device 10, continuing its task of testing, runs up to the end of the assigned path, and in that way, takes the lifted-up device 16 along with itself. After replacing tube 12 by a new one to be tested, the described procedure is repeated in reverse order, so that, in the end, transducer device 10 and the holding down device 16 are in their original positions again.

Clearly various obvious modifications can be made in the described system by those familiar with such systems. For instance, to provide data for its control a plurality of detection devices could be located along the test course for detecting the locations of the pressing means and transducer system.

What is claimed is:

1. Testing apparatus for elongated test specimens having an essentially circular cross-section, said apparatus having rollers supporting a test specimen from below and at least one of which being driven for rotating the test specimen about its central longitudinal axis, a transducer system for non-destructive testing of the test specimen including a transducer arrangement, a guiding arrangement to which the transducer arrangement is suspended, the structure of said guiding arrangement presetting a course or testing track along the test specimen in its longitudinal direction, means for moving the transducer arrangement in its course, and vertical positionable means for pressing the test specimens in its lowered condition onto the rollers, comprising:

a plurality of pressing means arranged movably in a direction longitudinally of the test specimen, each said pressing means located immediately adjacent the guiding arrangement, at least one before and one behind the transducer system, and means for selectively and releasably coupling each of the pressing means to the transducer system such that the pressing means moves unitarily with the transducer system when so-coupled.

2. Testing apparatus as in claim 1, in which upon the transducer system moving forward, a first pressing means is coupled to the rear of the transducer system and is lifted upwardly away from the test specimen, while simultaneously a second pressing means is deposited onto the test specimen at a predetermined roller, and after the transducer system arrives at the predetermined roller, the first pressing means is decoupled and lowered, and the second pressing means is lifted and coupled to the front of the transducer system for movement therewith.

3. Testing apparatus as in claim 2, in which the transducer system together with the two pressing means ccontinues its course until the first pressing means arrives at the predetermined roller locating at which time decoupling and lowering of the first pressing means to the test specimen occurs, while the transducer system moves on.

4. Testing devices as in claim 3, in which the transducer system exerts a pressure on the test specimen and while the first and second pressing means are in lifted up condition the test specimen presses onto the driven roller.

5. Testing device as in claim 4, in which the pressure exerted on the test specimen by the transducer system is adjustable.

6. Testing device as in either of claims 2 or 3, in which a return of the transducer system takes place in an opposite direction to the moving forward, during which lifting, lowering, decoupling, and coupling of the pressing means occur in reversed order to the order in which they occurred during forward movement.

7. Testing device as in either of claims 2 or 3, in which a braking device is provided for each pressing means for holding stationary when activated the blocking means for which it was provided.

8. Testing device as in either of claims 2 or 3, in which detection devices are arranged along the test course for detecting the locations of the pressing means and transducer system for controlling operation.

* * * * *